United States Patent
Friesen et al.

(10) Patent No.: US 6,448,274 B2
(45) Date of Patent: Sep. 10, 2002

(54) FLUOROALKOXY-SUBSTITUTED BENZAMIDE DICHLOROPYRIDINYL N-OXIDE PDE4 INHIBITOR

(75) Inventors: Richard Friesen, Kirkland; Yves Ducharme, Montreal; Yves Girard, L'ille Bizard; Chun Li, Kirkland; Annette Robichoud, Montreal, all of (CA)

(73) Assignee: Merck Frosst Canada & Co., Kirkland (CA)

(*) Notice: Subject to any disclaimer, the term of this patent is extended or adjusted under 35 U.S.C. 154(b) by 0 days.

(21) Appl. No.: 09/864,943

(22) Filed: May 24, 2001

Related U.S. Application Data

(60) Provisional application No. 60/207,023, filed on May 25, 2000.

(51) Int. Cl.[7] ............... A61K 31/44; A61K 31/4412; C07D 213/75
(52) U.S. Cl. ............................ 514/352; 546/309
(58) Field of Search ............................ 514/352; 546/309

(56) References Cited

U.S. PATENT DOCUMENTS

| | | |
|---|---|---|
| 5,340,827 A | 8/1994 | Beeley et al. |
| 5,491,147 A | 2/1996 | Boyd et al. |
| 5,550,137 A | 8/1996 | Beeley et al. |
| 5,580,888 A | 12/1996 | Warrellow et al. |
| 5,608,070 A | 3/1997 | Alexander et al. |
| 5,622,977 A | 4/1997 | Warrellow et al. |
| 5,633,257 A | 5/1997 | Warrellow et al. |
| 5,679,712 A | 10/1997 | Schwark et al. |
| 5,693,672 A | 12/1997 | Weichert et al. |
| 5,712,298 A | 1/1998 | Amschler |
| 5,736,297 A | 4/1998 | Roeschert et al. |
| 5,739,144 A | 4/1998 | Warrellow et al. |
| 5,747,541 A | 5/1998 | Weichert et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow |
| 5,849,770 A | 12/1998 | Head et al. |
| 5,859,034 A | 1/1999 | Warrellow et al. |
| 5,866,593 A | 2/1999 | Warrellow et al. |
| 5,891,896 A | 4/1999 | Warrellow et al. |

FOREIGN PATENT DOCUMENTS

| | | |
|---|---|---|
| EP | 811610 | 12/1997 |
| WO | WO 94/22852 | 10/1994 |
| WO | WO 95/35283 | 12/1995 |
| WO | WO 96/00215 | 1/1996 |
| WO | WO 98/25883 | 6/1998 |
| WO | WO 98/35683 | 8/1998 |

OTHER PUBLICATIONS

C. Burnouf, et al., Ann. Rep. In Med. Chem., vol. 33, pp. 91–109, 1998.
S. B. Christensen, et al., J. Med. Chem., vol. 41, pp. 821–835, 1998.
A. H. Cook, et al., J. Chem. Soc., pp. 413–417, 1943.
M. D. Houslay, et al., Adv. In Pharmacol., vol. 44, pp. 225–342, 1998.
B. Hughes, et al., Br. J. Pharmacol., vol. 118, pp. 1183–1191, 1996.
K. Manabe, et a., J. Am Chem., vol. 114(17, pp. 6940–6941, 1992.
K. Manabe, et al., J. Org. Chem., vol. 58(24, pp. 6692–6700, 1993.
K. Manabe, et al., J. Am. Chem. Soc., vol. 115(12), pp. 5324–5325, 1993.
M. J. Perry, et al., Cell Biochem. Biophys., vol. 29, pp. 113–132, 1998.
D. Spina, et al., Adv. In. Pharmacol., vol. 44, pp. 33–89, 1998.

*Primary Examiner*—Patricia L. Morris
(74) *Attorney, Agent, or Firm*—Shu M. Lee; David L. Rose

(57) ABSTRACT

A PDE4 inhibiting compound is represented by

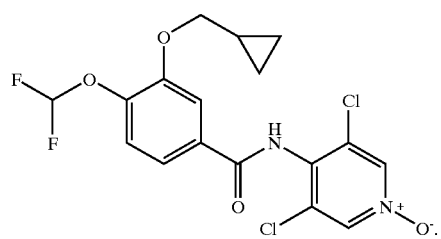

2 Claims, No Drawings

FLUOROALKOXY-SUBSTITUTED BENZAMIDE DICHLOROPYRIDINYL N-OXIDE PDE4 INHIBITOR

The present application claims the benefit of U.S. patent application No. 60/207,023, filed May 25, 2000.

BACKGROUND OF THE INVENTION

1. Field of the Invention

The present invention is directed to a fluoroalkoxy-substituted benzamide dichloropyridinyl N-oxide compound that is a phosphodiesterase-4 inhibitor. In particular, this invention is directed to N-(3,5-Dichloro-1-oxido-pyridin-4-yl)-4-difluoromethoxy-3-cyclopropylmethoxybenzamide which is a phosphodiesterase-4 inhibitor.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

Inhibition of PDE4 activity is believed effective for the treatment of osteoporosis by reducing bone loss. For example, Ken-ici Miyamoto et al., Biochem. Pharmacology, 54:613–617(1997) describes the effect of a PDE4 on bone loss. Therefore, it would be desirable to provide novel compounds and compositions that inhibit PDE4 activity.

A major concern with the use of PDE4 inhibitors is the side effect of emesis which has been observed for several candidate compounds as described in C.Burnouf et al., ("Burnouf"), Ann. Rep. In Med. Chem., 33:91–109(1998). B.Hughes et al., Br. J.Pharmacol., 118:1183–1191(1996); M. J. Perry et al., Cell Biochem. Biophys., 29:113–132 (1998); S. B. Christensen et al., J.Med. Chem., 41:821–835 (1998); and Burnouf describe the wide variation of the severity of the undesirable side effects exhibited by various compounds. As described in M. D. Houslay et al., Adv. In Pharmacol., 44:225–342(1998) and D.Spina et al., Adv. In Pharmacol., 44:33–89(1998), there is great interest and research of therapeutic PDE4 inhibitors.

Fluoroalkoxy-substituted Benzamide PDE4 inhibitors are described in U.S. Pat. No. 5,712,298 and International Publication No. WO 98/35683.

International Patent Publication WO9422852 describes quinolines as PDE4 inhibitors. A. H. Cook, et al., J.Chem. Soc., 413–417(1943) describes gamma-pyridylquinolines. Other quinoline compounds are described in Kei Manabe et al., J.Org. Chem., 58(24):6692–6700(1993); Kei Manabe et al., J.Am. Chem. Soc., 115(12):5324–5325(1993); and Kei Manabe et al., J.Am. Chem. Soc., 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

A compound of this invention is represented by Formula (I):

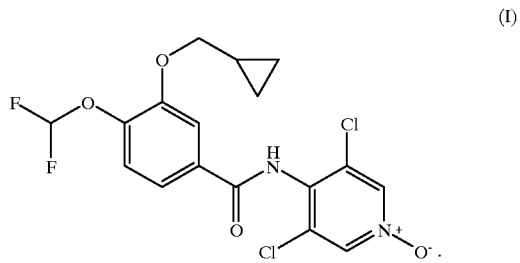

(I)

A method of treatment of asthma, chronic bronchitis, chronic obstructive pulmonary disease, eosinophilic granuloma, psoriasis and other benign or malignant proliferative skin diseases, endotoxic shock, laminitis in horses, colic in horses, septic shock, ulcerative colitis, Crohn's disease, reperfusion injury of the myocardium and brain, inflammatory arthritis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, osteoporosis, ankylosing spondylitis, transplant rejection, graft versus host disease, hypersecretion of gastric acid, bacterial, fungal induced sepsis, viral induced sepsis, fungal induced septic shock, viral induced septic shock, inflammation-mediated chronic tissue degeneration, cytokine-mediated chronic tissue degeneration, osteoarthritis, cancer, cachexia, muscle wasting, depression, memory impairment, tumor growth, or cancerous invasion of normal tissues comprises the step of administering a therapeutically effective amount of a compound represented by Formula (I):

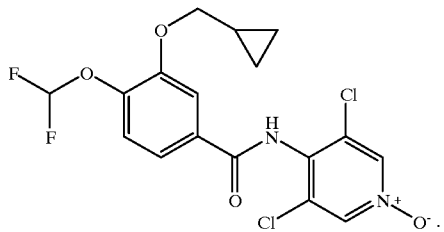

(I)

DETAILED DESCRIPTION OF THE INVENTION

A compound of this invention is represented by Formula (I):

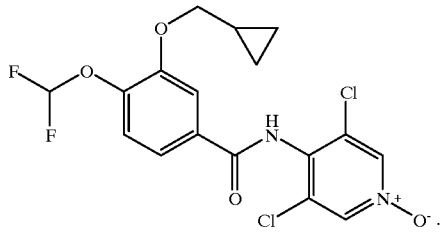

(I)

The compound of Formula (I) ("Compound I") is made from precursor compound II represented by Formula (II):

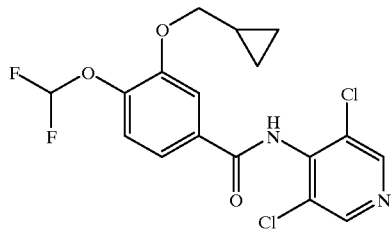

(II)

available from BYK Gulden Lomberg Chemische Fabrik GmbH, Konstanz, Germany. Compound II is itself a PDE4 inhibitor. However, Compound (I) has pharmacokinetics that are very different from Compound (II). Further, the PDE4 inhibitory parameters and the brain barrier interaction of Compound (I) differ substantially from that of Compound (II). In particular, as shown below, the properties of Compound (I) with regard the brain barrier are unexpectedly superior to those properties demonstrated by Compound (II).

Compounds having PDE 4 inhibitory activity can be characterized using the following assay protocols.

Assays for Determining PDE 4 Inhibitory Activity
SPA Based PDE Activity Assay Protocol Compounds which inhibit the hydrolysis of cAMP to AMP by the type-IV cAMP-specific phosphodiesterases were screened in 96-well plate format as follows:

In a 96 well-plate at 30° C. was added the test PDE 4 inhibitory compound (dissolved in 2μl DMSO), 188 ml of substrate buffer containing [2,8-$^3$H] adenosine 3',5'-cyclic phosphate (cAMP, 100 nM to 50 μM), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min. at 30° C.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit of the standard 4-parameter/multiple binding sites equation from a ten point titration.

LPS and fMLP-Induced TNF-α and $LTB_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and $LTB_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. $LTB_4$ synthesis is also sensitive to levels of intracellular cAMP and can be completely inhibited by PDE4-selective inhibitors. As there is little $LTB_4$ produced during a 24 hour LPS stimulation of whole blood, an additional LPS stimulation followed by fMLP challenge of human whole blood is necessary for $LTB_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from *E. coli*, serotype 011:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10μL of fMLP (1 μM final concentration, #F-3506 (Sigma); diluted in 1% w/v BSA (in PBS)) for 15 minutes at 37° C. The blood samples were centrifuged at 1500 xg for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The $IC_{50}$ values of Examples 1–42 generally ranged from 0.04 μM to 8.71 μM.

Effect on Duration of Anesthesia

Compound I of the present invention was compared to Compound II by testing the for effects on the duration of anesthesia induced by the combination of xylazine and ketamine in rats. Male Sprague-Dawley rats were anaesthetised with a combination of xylazine (10 mg/kg) and ketamine (10 mg/kg) administered in a single intramuscular injection in the back hindlimb. Fifteen minutes later, the drug to be tested or its vehicle was injected intraperitoneally (dosing volume=1 ml/kg) and the animals were placed in dorsal recumbence. The compounds were dissolved immediately before use in polyethylene glycol (M.W. 200). The return of the righting reflex (i.e. when the animal no longer remained on its back and turned itself spontaneously to the prone position) was used as an endpoint to determine the duration of anaesthesia.

At the end of the experiment, at 60 minutes post-dosing, plasma and brain samples were taken for drug concentration determination. Referring to Table 1 below, administration of Compound I (3 mg/kg i.p, n=5) did not significantly modify the duration of anaesthesia. By contrast, the administration of Compound II (3 mg/kg i.p., n=5) led to a significant reduction in the duration of the anaesthesia induced by the combination of xylazine/ketamine.

TABLE 1

Effect of Compounds I and II on the duration of anesthesia induced by the combination of xylazine and ketamine in rats. Results are expressed as mean ± S.E.M.

| Treatment (3 mg/kg, i.p.) | Vehicle treated group (n = 8–9) | Compound treated group (n = 5) | Inhibition % |
|---|---|---|---|
| | Duration of anesthesia (min) | | |
| Compound Formula I | 44.33 ± 4.81 | 37.40 ± 7.83 | 15.6 |
| Compound Formula II | 42.38 ± 4.98 | 19.20 ± 4.68 | 54.7 |

Referring to Table 2 below, analysis of the plasma and brain samples revealed that both compounds were absorbed. However, the distribution to the brain was very different for each compound. Consistent with the in vivo data on the duration of anaesthesia, Compound Formula I was found to be less brain permeable than compound of Formula II.

TABLE 2

Plasma and brain concentrations of Compounds I and II

| Compound | Plasma (μM) | Brain (μM) | Brain/plasma % | n |
|---|---|---|---|---|
| Compound Formula I | 4.37 ± 1.65 | 0.41 ± 0.15 | 9.38 | 5 |
| Compound Formula II | 0.20 ± 0.08 | 0.15 ± 0.05 | 75 | 5 |

Accordingly, while disadvantageously Compound II readily crosses the brain barrier, Compound (I) unexpected and advantageously does not readily cross the brain barrier.

Compound (I) can be made according to the following procedure shown in Scheme I:

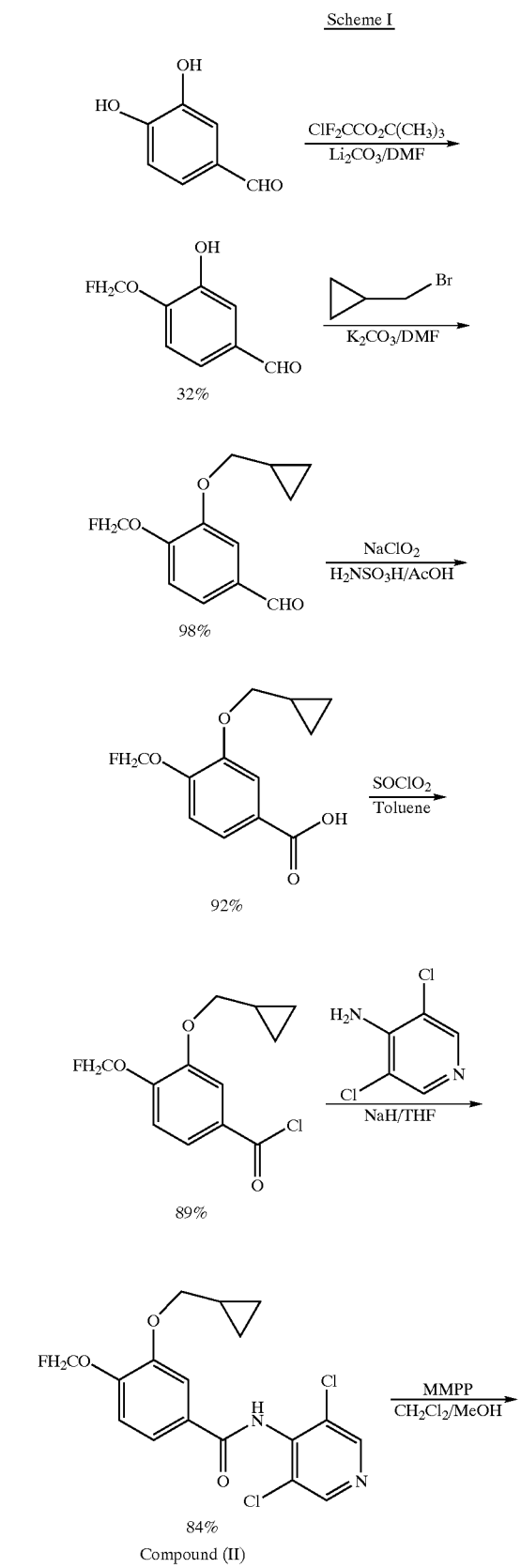

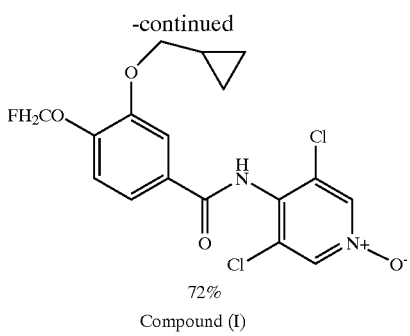

72%
Compound (I)

The synthesis of Compound (II) is described in U.S. Pat. No. 5,712,298 and the compound is available from BYK Gulden (Konstanz, Germany). Compound I was obtained from Compound II by the following procedure:

EXAMPLE 1-COMPOUND I

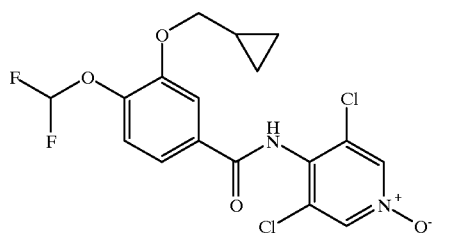

N-(3,5-Dichloro-1-oxido-pyridin-4-yl)-4-difluoromethoxy-3-cyclopropylmethoxybenzamide A mixture of N-(3,5-Dichloropyridin-4-yl)-4-difluoromethoxy-3-cyclopropylmethoxybenzamide (3.0 g, 7.4 mmol) and magnesium monoperoxyphthalate hexahydrate ("MMPP") (7.36 g, 14.9 mmol) in $CH_2Cl_2$/MeOH (10 mL) was stirred under reflux for 48 h. An additional amount of magnesium monoperoxyphthalate hexahydrate (7.4 g, 15 mmol) was added and the reaction mixture was stirred under reflux for an additional 24 h. Ethyl acetate was then added and the organic phase was washed by 25% aqueous $NH_4OAc$, water and brine, dried ($MgSO_4$) and concentrated. The residue was purified by column chromatography on silica (EtOAc) to yield N-(3.5-Dichloro-1-oxido-pyridin-4-yl)-4-difluoromethoxy-3-cyclopropylmethoxybenzamide (Compound I) as a white solid (1.98 g, 63%). $^1$H NMR (500 MHz, acetone-$d_6$): δ 0.40 (m, 2H), 0.60 (m, 2H), 1.30 (m, 1H), 4.0 (d, 2H), 7.05 (t, 1H), 7.35 (d, 1H), 7.7 (m, 1H), 7.75 (s, 1H), 8.40 (s, 2H), 9.6 (bs, 1H).

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, and iii) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of conditions such as asthma, chronic bronchitis, chronic obstructive pulmonary disease, eosinophilic granuloma, psoriasis and other benign or malignant proliferative skin diseases, endotoxic shock, laminitis in horses, colic in horses, septic shock, ulcerative colitis, Crohn's disease, reperfusion injury of the myocardium and brain, inflammatory arthritis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, osteoporosis, ankylosing spondylitis, transplant rejection, graft versus host disease, hypersecretion of gastric acid, bacterial, fungal induced sepsis, viral induced sepsis, fungal induced septic shock, viral induced septic shock, inflammation-mediated chronic tissue degeneration, cytokine-mediated chronic tissue degeneration, osteoarthritis, cancer, cachexia, muscle wasting, depression, memory impairment, tumor growth, or cancerous invasion of normal tissues which are responsive to PDE4 inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 mg to about 3.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compound represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compound of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease, eosinophilic granuloma, psoriasis and other benign or malignant proliferative skin diseases, endotoxic shock, laminitis in horses, colic in horses, septic shock, ulcerative colitis, Crohn's disease, reperfusion injury of the myocardium and brain, inflammatory arthritis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, osteoporosis, ankylosing spondylitis, transplant rejection, graft versus host disease, hypersecretion of gastric acid, bacterial, fungal induced sepsis, viral induced sepsis, fungal induced septic shock, viral induced septic shock, inflammation-mediated chronic tissue degeneration, cytokine-mediated chronic tissue degeneration, osteoarthritis, cancer, cachexia, muscle wasting, depression, memory impairment, tumor growth, or cancerous invasion of normal tissues—maladies that are amenable to amelioration through inhibition of the PDE4 isoenzyme and the resulting elevated cCAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, or iii) M2/M3 antagonists.

Other variations or modifications, which will be obvious to those skilled in the art, are within the scope and teachings of this invention. This invention is not to be limited except as set forth in the following claims.

What is claimed is:

1. A compound represented by Formula (I):

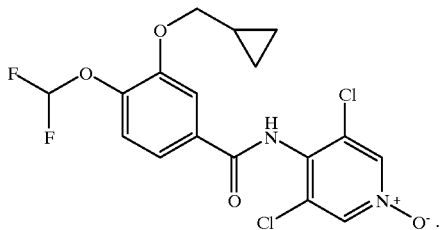

(I)

2. A pharmaceutical composition comprising a therapeutically effective amount of
   the compound according to claim 1 or a pharmaceutically acceptable salt thereof; and
   a pharmaceutically acceptable carrier.

* * * * *